United States Patent
Muller et al.

(10) Patent No.: US 6,429,221 B1
(45) Date of Patent: *Aug. 6, 2002

(54) SUBSTITUTED IMIDES

(75) Inventors: George W. Muller, Bridgewater; Mary Shire, North Plainfield; David I. Stirling, Branchburg, all of NJ (US)

(73) Assignee: Celgene Corporation, Warren, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/366,679

(22) Filed: Dec. 30, 1994

(51) Int. Cl.$^7$ .................. A61K 31/42; A61K 31/40; C07D 209/48; C07D 209/46
(52) U.S. Cl. .................. 514/375; 514/417; 548/476; 548/472; 548/477; 548/479
(58) Field of Search ................ 514/375, 417; 548/476, 472, 477, 479

(56) References Cited

U.S. PATENT DOCUMENTS 5,703,098 A * 12/1997 Muller et al. ............ 514/339
5,728,844 A * 3/1998 Muller et al. ............ 548/472

OTHER PUBLICATIONS

Rao et al, 1992, 117CA: 171706y.*
Kawagishi et al, 1992, 117CA: 20027b.*
Nagaoka et al 1989, 110CA:38880q.*
Sasaki, et al Biol Pham Bull. vol. 17(9) pp. 1313–1315 1994.*
Sugimoto et al 108 CA 112237n, 1988.*
Kawagishi et al 112 CA 195294k, 1990.*
F. Bachelerie et al. Apr. 25, 1991 *Nature*, vol. 350, pp. 709–712.
Debajit K. Biswas et al. (1993) *Journal of Acquired Immune Deficiency Syndromes*, vol. 6, pp. 778–786.
Ghassan S. Dbaibo et al. Aug. 25, 1993 *The Journal of Biological Chemistry*, vol. 265 (24), pp. 17762–17766.
Elia J. Duh et al. Aug. 1989 *Proc. Natl. Acad. Sci. USA*, vol. 86, pp. 5974–5978.
Alexander N. Shakhov et al. Jan. 1990*J. Exp. Med.*, vol. 171, pp. 35–47.
Frank J. T. Staal et al. Dec. 1990 *Proc. Natl. Acad. Sci. USA*, vol. 87, pp. 9943–9947.
Yuichiro J. Suzuki et al. Dec. 30, 1992 *Biochemical and Biophysical Research Communictions*, vol. 189 (3) , pp. 1709–1715.
Yuichiro J. Suzuki et al. May 28, 1993 *Biochemical and Biophysical Research Communications*, vol. 193 (1), pp. 277–283.
Yuichiro J. Suzuki et al. (Nov. 1993) *Biochemistry and Molecular Biology International*, vol. 31 (4), pp. 693–700.

* cited by examiner

*Primary Examiner*—Russell Travers
(74) *Attorney, Agent, or Firm*—Mathews, Collins, Shepherd & Gould, P.A.

(57) ABSTRACT

Novel imides are inhibitors of tumor necrosis factor α and can be used to combat cachexia, endotoxic shock, and retrovirus replication. A typical embodiment is 2-Phthalimido-3-(3',4'-dimethoxyphenyl)propane.

18 Claims, No Drawings

SUBSTITUTED IMIDES

BACKGROUND OF THE INVENTION

The present invention relates a method of reducing levels of TNFα in a mammal and to compounds and compositions useful therein.

TNFα, or tumor necrosis factor α, is a cytokine which is released primarily by mononuclear phagocytes in response to various immunostimulators. When administered to animals or humans it causes inflammation, fever, cardiovascular effects, hemorrhage, coagulation and acute phase responses similar to those seen during acute infections and shock states.

Excessive or unregulated TNFα production has been implicated in a number of disease conditions. These include endotoxemia and/or toxic shock syndrome {Tracey et al., *Nature* 330, 662-664 (1987) and Hinshaw et al., *Circ. Shock* 30, 279–292 (1990)}; cachexia {Dezube et al., *Lancet*, 335(8690), 662 (1990)}; and Adult Respiratory Distress Syndrome where TNFα concentration in excess of 12,000 pg/milliliters have been detected in pulmonary aspirates from ARDS patients {Millar et al., *Lancet* 2(8665), 712–714 (1989)}. Systemic infusion of recombinant TNFα also resulted in changes typically seen in ARDS {Ferrai-Baliviera et al., *Arch Surg.* 124(12), 1400–1405 (1989)}.

TNFα appears to be involved in bone resorption diseases, including arthritis where it has been determined that when activated, leukocytes will produce a bone-resorbing activity, and data suggest that TNFα contributes to this activity. {Bertolini et al, *Nature* 319, 516–518 (1986) and Johnson et al, *Endocrinology* 124(3), 1424–1427 (1989).} It has been determined that TNFα stimulates bone resorption and inhibits bone formation in vitro and in vivo through stimulation of osteoclast formation and activation combined with inhibition of osteoblast function. Although TNFα may be involved in many bone resorption diseases, including arthritis, the most compelling link with disease is the association between production of TNFα by tumor or host tissues and malignancy associated hypercalcemia {*Calci. Tissue Int.* (US) 46(Suppl.), S3–10 (1990)}. In Graft versus Host Reaction, increased serum TNFα levels have been Rated with major complication following acute allogenic bone marrow transplants {Holler et at, *Blood*, 75(4), 1011–1016 (1990)}.

Cerebral malaria is a lethal hyperacute neurological syndrome associated with high blood levels of TNFα and the most severe complication occurring in malaria patients. Levels of serum TNFα correlated directly with the severity of disease and the prognosis in patients with acute malaria attacks {Grau et al., *N. Engl. J. Med*, 320(24), 1586–1591 (1989)}.

TNFα also plays a role in the area of chronic pulmonary inflammatory diseases. The deposition of silica particles leads to silicosis, a disease of progressive respiratory failure caused by a fibrotic reaction. Antibody to TNFα completely blocked the silica-induced lung fibrosis in mice {Pignet et al., *Nature*, 344:245–247 (1990)}. High levels of TNFα production (in the serum and in isolated macrophages) have been demonstrated in animal models of silica and asbestos induced fibrosis {Bissonnette et al., *Inflammation* 13(3), 329–339 (1989)}. Alveolar macrophages from pulmonary sarcoidosis patients have also been found to spontaneously release massive quantities of TNFα as compared with macrophages from normal donors {Baughman et al., *J. Lab. Clim Med.* 115(1), 36–42 (1990)}.

TNFα is also implicated in the inflammatory response which follows reperfusion, called reperfusion injury, and is a major cause of tissue damage after loss of blood flow {Vedder et al., *PNAS* 87, 2643–2646 (1990)}. TNFα also alters the properties of endothelial cells and has various pro-coagulant activities, such as producing an increase in tissue factor pro-coagulant activity and suppression of the anticoagulant protein C pathway as well as down-regulating the expression of thrombomodulin {Sherry et at, *J. Cell Biol.* 107, 1269–1277 (1988)}. TNFα has pro-inflammatory activities which together with its early production (during the initial stage of an inflammatory event) make it a likely mediator of tissue injury in several important disorders including but not limited to, myocardial infarction, stroke and circulatory shock. Of specific importance may be TNFα-induced expression of adhesion molecules, such as intercellular adhesion molecule (ICAM) or endothelial leukocyte adhesion molecule (ELAM) on endothelial cells {Munro et al., *Am. J. Path.* 135(1), 121–132 (1989)}. Moreover, it now is known that TNFα is a potent activator of retrovirus replication including activation of HIV-1. {Duh et al., *Proc. Nat. Acad. Sci.* 86, 5974–5978 (1989); Poll et al., *Proc. Nat. Acad. Sci.* 87, 782–785 (1990); Monto et al., *Blood* 79, 2670 (1990); Clouse et al., *J. Immunol.* 142, 431–438 (1989); Poll et al., *AIDS Res. Hum. Retrovirus*, 191–197 (1992)}. AIDS results from the infection of T lymphocytes with Human Immunodeficiency Virus (HIV). At least three types or strains of HIV have been identified, Le., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T lymphocyte activation. Therefore, interference with cytokine activity such as by prevention or inhibition of cytokine production, notably TNFα, in an HIV-infected individual aids in limiting the maintenance of T lymphocyte caused by HIV infection.

Monocytes, macrophages, and related cells, such as kupffer and glial cells, have also been implicated in maintenance of the HIV infection. These cells, like T cells, are targets for viral replication and the level of viral replication is dependent upon the activation state of the cells. {Rosenberg et al, *The Immunopathogenesis of HIV Infection*, Advances in Immunology, 57 (1989)}. Cytokines, such as TNFα, have been shown to activate HIV replication in monocytes and/or macrophages {Poli et al. *Proc. Natl. Acad. Sci.*, 87, 782–784 (1990)}, therefore, prevention or inhibition of cytokine production or activity aids in limiting HIV progression as stated above for T cells. Additional studies have identified TNFα as a common factor in the activation of HIV in vitro and has provided a clear mechanism of action via a nuclear regulatory protein found in the cytoplasm of cells (Osborn, et al., *PNAS* 86, 2336–2340). This evidence suggests that a reduction of TNFα synthesis may have an antiviral effect in HIV infections by reducing the transcription and thus virus production.

AIDS viral replication of latent HIV in T cell and macrophage lines can be induced by TNFα {Folks et al., *PNAS* 86, 2365–2368 (1989)}. A molecular mechanism for the virus inducing activity is suggested by TNFα's ability to activate a gene regulatory protein (NFκB) found in the cytoplasm of cells, which promotes HIV replication through binding to a viral regulatory gene sequence (LTR) {Osborn et al., PNAS 86, 2336–2340 (1989)}. TNFα in AIDS and cancer associated cachexia is suggested by elevated serum TNFα and high levels of spontaneous TNFα production in peripheral blood monocytes from patients {Wright et al. J. Immunol. 141(1), 99–104 (1988)}. Eur J. Gastroen Hepat 6(9), 821–829, 1994.

TNFα has been implicated in various roles with other viral infections, such as the cytomegalia virus (CMV), influenza virus, adenovirus, and the herpes family of viruses for similar reasons as those noted.

Preventing or inhibiting the production or action of TNFα is, therefore, predicted to be a potent therapeutic strategy for many inflammatory, infectious, immunological or malignant diseases. These include but are not restricted to septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis, other arthritic conditions, Crohn's disease, ulcerative colitis, multiple sclerosis, systemic lupus erythrematosis, ENL in leprosy, radiation damage, and hyperoxic alveolar injury. Efforts directed to the suppression of the effects of TNFα have ranged from the utilization of steroids such as dexamethasone and prednisolone to the use of both polyclonal and monoclonal antibodies {Beutler et al., Science 234, 470–474 (1985); WO 92/11383}. (Clinical and Experimental Rheumatology 1993, 11 (Suppl. 8), 5173–5175). (PNAS 1992, 89, 9784–88). (Annals of the Rheumatic Diseases 1990, 49, 480–486).

The nuclear factor κB (NEκB) is a pleiotropic transcriptional activator (Lenardo, et al. Cell 1989, 58, 227–29). NFκB has been implicated as a transcriptional activator in a variety of disease and inflammatory states and is thought to regulate cytokine levels including but not limited to TNFα and also to be an activator of HIV transcription (Dbaibo, et al. J. Biol. Chem. 1993, 17762–66; Duh et al. Proc. Natl. Acad. Sci. 1989, 86, 5974–78; Bachelerie et al. Nature 1991, 350, 709–12; Boswas et al. J. Acquired Immune Deficiency Syndrome 1993, 6, 778–786; Suzuki et al. Biochem. And Biophys. Res. Comm. 1993, 193, 277–83; Suzuki et al. Biochem. And Biophys. Res Comm. 1992, 189, 1709–15; Suzuki et a., Biochem. Mol. Bio. Int. 1993, 31(4), 693–700; Shakhov et al. 1990, 171, 35–47; and Staal et al Proc. Natl. Acad. Sci. USA 1990, 87, 9943–47). Thus, inhibition of NFκB binding can regulate transcription of cytokine gene(s) and through this modulation and other mechanisms be useful in the inhibition of a multitude of disease states. The compounds claimed in this patent can inhibit the action of NFκB in the nucleus and thus are useful in the treatment of a variety of diseases including but not limited to rheumatoid arthritis, rheumatoid spondylitis, osteoarthritis, other arthritic conditions, septic shock, septis, endotoxic shock, graft versus host disease, wasting, Crohn's disease, ulcerative colitis, multiple sclerosis, systemic lupus erythrematosis, ENL in leprosy, HIV, AIDS, and opportunistic infections in AIDS.

TNFα and NFκB levels are influenced by a reciprocal feedback loop. As noted above, the compounds of the present invention affect the levels of both TNFα and NFκB. It is not known at this time, however, how the compounds of the present invention regulate the levels of TNFα, NFκB, or both.

DETAILED DESCRIPTION

The present invention is based on the discovery that a class of non-polypeptide imides more fully described herein appear to inhibit the action of TNFα.

The present invention pertains to compounds of the formula:

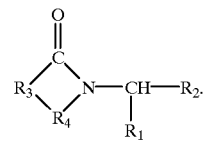

I in which:

$R^1$ is (i) straight, branched, or cyclic alkyl of 1 to 12 carbon atoms, (ii) phenyl or phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, straight or branched alkyl of 1 to 10 carbon atoms, alkoxy of 1 to 10 carbon atoms, or halo, (iii) benzyl or benzyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, or (iv) —Y—Ph where Y is a straight, branched, or cyclic alkyl of 1 to 12 carbon atoms and Ph is phenyl or phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo;

$R^2$ is —H, a branched or unbranched alkyl of 1 to 10 carbon atoms, phenyl, pyridyl, heterocycle, —CH$_2$—Aryl, or —CH$_2$—heterocycle;

$R^3$ is i) ethylene, ii) vinylene, iii) a branched alkylene of 3 to 10 carbon atoms, iv) a branched alkenylene of 3 to 10 carbon atoms, v) cycloalkylene of 4 to 9 carbon atoms unsubstituted or substituted with 1 to 2 substituents each selected independently from nitro, cyano, trifluoromethyl, carbethoxy, carbomethoxy, carbopropoxy, acetyl, carbamoyl, acetoxy, carboxy, hydroxy, amino, substituted amino, alkyl of 1 to 4 carbon atoms, alkoxy of 1 to 4 carbon atoms, or halo, vi) cycloalkenylene of 4 to 9 carbon atoms unsubstituted or substituted with 1 to 2 substituents each selected independently from nitro, cyano, trifluoromethyl, carbethoxy, carbomethoxy, carbopropoxy, acetyl, carbamoyl, acetoxy, carboxy, hydroxy, amino, substituted amino, alkyl of 1 to 4 carbon atoms, alkoxy of 1 to 4 carbon atoms, or halo, or vii) o-phenylene unsubstituted or substituted with 1 to 2 substituents each selected independently from nitro, cyano, trifluoromethyl, carbethoxy, carbomethoxy, carbopropoxy, acetyl, carbamoyl, acetoxy, carboxy, hydroxy, amino, substituted amino, alkyl of 1 to 4 carbon atoms, alkoxy of 1 to 4 carbon atoms, or halo; and, $R^4$ is —CX, or —CH$_2$—;

X is O or S.

The term alkyl as used herein denotes a univalent saturated branched or straight hydrocarbon chain. Unless otherwise stated, such chains can contain from 1 to 18 carbon atoms. Representative of such alkyl groups are methyl, ethyl, propyl, isopropyl, butyl, isobutyl, sec-butyl, tert-butyl, pentyl, isopentyl, neopentyl, tert-pentyl, hexyl, isohexyl, heptyl, octyl, nonyl, decyl, undecyl, dodecyl, tridecyl, tetradecyl, pentadecyl, hexadecyl, heptadecyl, octadecyl, and the like. When qualified by "lower", the alkyl group will contain from 1 to 6 carbon atoms. The same carbon content applies to the parent term "alkane" and to derivative terms such as "alkoxy".

The compounds can be prepared using methods which are known in general for the preparation of imides. General reaction schemes include the reaction of the substituted amine with either phthalic anhydride, N-carbethoxyphthalimide, 1,2-benzenedicarbaldehyde or various substituted anhydrides as illustrated by the formulas:

A.

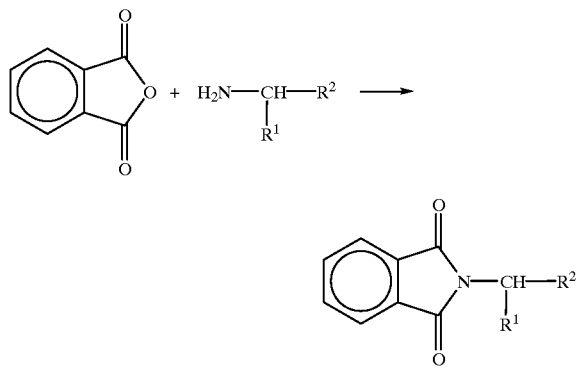

B.

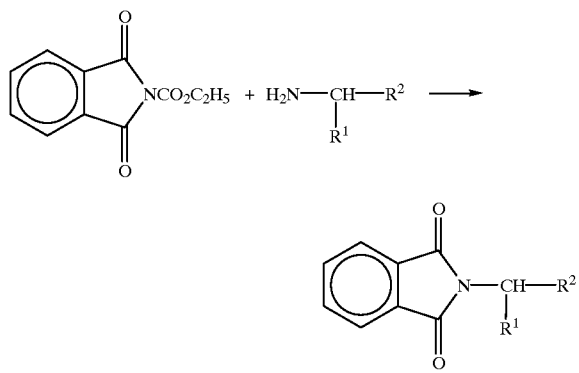

C.

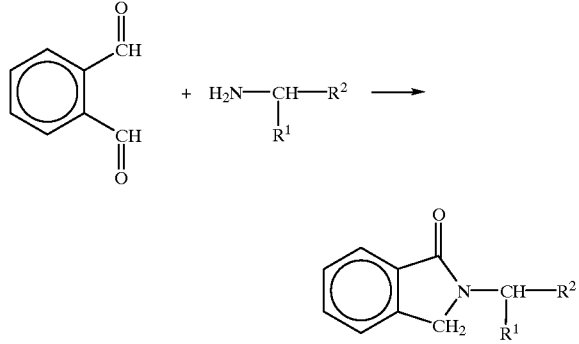

D.

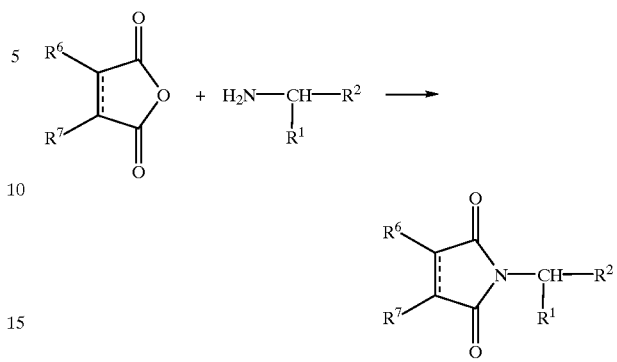

$R^6$ and $R^7$ are hydrogen, nitro, cyano, trifluoromethyl, carbethoxy, carbomethoxy, carbopropoxy, acetyl, carbamoyl, acetoxy, carboxy, hydroxy, amino, substituted amino, alkyl of 1 to 4 carbon atoms, alkoxy of 1 to 4 carbon atoms, halo or $R^6$ and $R^7$ together with the carbons to which they are attached represent a cycloalkylene ring of 4 to 9 carbon atoms unsubstituted or substituted with one or more substituents each selected independently from nitro, cyano, trifluoromethyl, carbethoxy, carbomethoxy, carbopropoxy, acetyl, carbamoyl, acetoxy, carboxy, hydroxy, amino, substituted amino, alkyl of 1 to 4 carbon atoms, alkoxy of 1 to 4 carbon atoms, or halo.

A first preferred subclass of Formula I pertains to compounds in which:

$R^1$ is 3,4-diethoxyphenyl and 3,4-dimethoxyphenyl $R^3$ is o-phenylene substituted with amino; and, $R^4$ is —CO— or —CH$_2$—:

The compounds can be used, under the supervision of qualified professionals, to inhibit the undesirable effects of TNFα. The compounds can be administered orally, rectally, or parenterally, alone or in combination with other therapeutic agents including antibiotics, steroids, etc., to a mammal in need of treatment. Oral dosage forms include tablets, capsules, dragees, and similar shaped, compressed pharmaceutical forms. Isotonic saline solutions containing 20–100 milligrams/milliliter can be used for parenteral administration which includes intramuscular, intrathecal, intravenous and intra-arterial routes of administration. Rectal administration can be effected through the use of suppositories formulated from conventional carriers such as cocoa butter.

Dosage regimens must be titrated to the particular indication, the age, weight, and general physical condition of the patient, and the response desired but generally doses will be from about 1 to about 500 milligrams/day as needed in single or multiple daily administration. In general, an initial treatment regimen can be copied from that known to be effective in interfering with TNFα activity for other TNFα mediated disease states by the compounds of the present invention. Treated individuals will be regularly checked for T cell numbers and T4/T8 ratios and/or measures of viremia such as levels of reverse transcriptase or viral proteins, and/or for progression of cytokine-mediated disease associated problems such as cachexia or muscle degeneration. If no effect is found following the normal treatment regimen, then the amount of cytokine activity interfering agent administered is increased, e.g., by fifty percent a week.

The compounds of the present invention also can be used topically in the treatment or prophylaxis of topical disease states mediated or exacerbated by excessive TNFα production, respectively, such as viral infections, such as those caused by the herpes viruses, or viral conjunctivitis, etc.

The compounds also can be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anaemia virus, caprine arthritis virus, visna virus, and maedi virus, as well as other lentiviruses.

Certain of these compounds possess centers of chirality and can exist as optical isomers. Both the racemates of these isomers and the individual isomers themselves, as well as diastereomers when there are two chiral centers, are within the scope of the present invention. The racemates can be used as such or can be separated into their individual isomers mechanically as by chromatography using a chiral absorbent. Alternatively, the individual isomers can be prepared in chiral form or separated chemically from a mixture by forming salts with a chiral acid, such as the individual enantiomers of 10-camphorsulfonic acid, camphoric acid, alpha-bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as to obtain either or both substantially free of the other; i.e., in a form having an optical purity of >95%.

Prevention or inhibition of production of TNFα by these compounds can be conveniently assayed using anti-TNFα antibodies. For example, plates (Nunc Immunoplates, Roskilde, DK) are treated with 5 µg/milliliter of purified rabbit anti-TNFα antibodies at 4° C. for 12 to 14 hours. The plates then are blocked for 2 hours at 25° C. with PBS/0.05% Tween containing 5 milligrams/milliliter BSA. After washing, 100 µL of unknowns as well as controls are applied and the plates incubated at 4° C. for 12 to 14 hours. The plates are washed and assayed with a conjugate of peroxidase (horseradish) and mouse anti-TNFα monoclonal antibodies, and the color developed with o-phenylenediamine in phosphatecitrate buffer containing 0.012% hydrogen peroxide and read at 492 nm.

Typical compounds of this invention include:
1-phthalimido-1-(3',4'-diethoxyphenyl)ethane,
1-(1'-oxoisoindolinyl)-1-(3',4'-diethoxyphenyl)ethane,
1-phthalimido-1-(3',4'-diethoxyphenyl)propane,
1-(1'-oxoisoindolinyl)-1-(3',4'-diethoxyphenyl)propane,
1-phthalimido-1-(3',4'-diethoxyphenyl)butane,
1-(1'-oxoisoindolinyl)-1-(3',4'-diethoxyphenyl)butane,
1-phthalimido-1-(3',4'-diethoxyphenyl)-2-phenylethane,
1-(1'-oxoisoindolinyl)-1-(3',4'-diethoxyphenyl)-2-phenylethane,
1-phthalimido-1-(3',4'-diethoxyphenyl)-3-pyridylpropane,
1-(1-oxoisoindolinyl)-1-(3,4-diethoxyphenyl)-3-pyridylpropane,
1-phthalimido-1-(3',4'-diethoxyphenyl)-3-phenylpropane,
1-(1'-oxoisoindolinyl)-1-(3',4'-diethoxyphenyl)-3-phenylpropane,
1-phthalimido-1-(3',4'-diethoxyphenyl)-2-pyridylethane,
1-(1'-oxoisoindolinyl)-1-(3',4'-diethoxyphenyl)-2-pyridylethane,
1-phthalimido-1-(3',4'-diethoxyphenyl)butane,
1-(1'-oxoisoindolinyl)-1-(3',4'-diethoxyphenyl)butane,
1-phthalimido-1-(3',4'-diethoxyphenyl)-2-imidazolylethane,
1-(1'-oxoisoindolinyl)-1-(3',4'-diethoxyphenyl)-2-imidazolylethane,
1-phthalimido-1-(3',4'-diethoxyphenyl)-3-methylbutane,
1-(1'-oxoisoindolinyl)-1-(3',4'-diethoxyphenyl)-3-methylbutane.

The following examples will serve to further typify the nature of this invention but should not be construed as a limitation in the scope thereof, which scope is defined solely by the appended claims.

EXAMPLE 1

2-Phthalimido-3-(3,4-dimethoxyphenyl)propane

To a stirred solution of 3-(3,4-dimethoxyphenyl)-2-aminopropane (1.95 grams, 10.0 mmol) and sodium carbonate (1.06 grams, 10.0 mmol) in 50 milliliters of water was added N-carbethoxyphthalimide (2.19 grams, 10.0 mmol). After 10 minutes the reaction mixture was diluted with 40 milliliters of acetonitrile and the mixture stirred for 40 minutes The reaction solution was partially concentrated in vacuo to remove the acetonitrile. The resulting mixture of an oil and aqueous layer was extracted with methylene chloride (25 milliliters). The organic extract was dried over sodium sulfate and concentrated in vacuo to afford a crude product which was purified by flash chromatography to afford 1.73 grams (53%) of product as a thick oil which slowly solidified to a white wax: $^1$H NMR (dmso-$d_6$, 250 MHz) δ7.7 (m, 4 H, Ar), 6.7 (m, 3 H, Ar), 4.63 (m, 1 H, CH), 3.79 (s, 3 H, OMe), 3.73 (s, 3 H, OMe), 3.28 (dd, 1 H, J =13.8, 9.8 Hz), 3.03 (dd, J=13.8, 6.5 Hz, 1 H), 1.54 (d, J=6.9 Hz, 3 H); $^{13}$C NMR (dmso-$d_6$) δ168.4, 148.6, 147.4, 133.7, 131.8, 130.9, 122.9, 120.9, 111.1, 55.7, 55.6, 48.6, 39.3, 18.3. Anal. Calcd for $C_{19}H_{19}NO_2$. Theoretical C, 70.14; H, 5.89; N, 4.30. Found C, 70.08; H, 5.83; N, 4.30.

EXAMPLE 2

1-Phthalimido-1-(3',4'-dimethoxyphenyl)ethane a) 3',4'-Dimethoxyacetophenone oxime A solution of hydroxylamine hydrochloride (3.33 grams, 48 mmol) and sodium acetate (4.92 grams, 60 mmol) in 20 milliliters of water was added to a stirring solution of 3',4'-dimethoxyacetophenone (5.41 grams, 30.0 mmol) in a mixture of water (30 milliliters) and ethanol (30 milliliters), the solution was stirred overnight. The resulting mixture was filtered and the solid was dried in vacuo (60° C., <1 mm) to afford 4.68 grams (80%) of product as a yellow solid: mp 137–138° C.; $^1$H NMR (CDCl$_3$) δ7.34–7.08 (m, 2H), 6.94–6 80 (m, 1H), 3.92 (s, 3H ), 3.90 (s, 3H), 2.28 (s , 3H); $^{13}$C NMR (CDCl$_3$) δ155.6, 150.1, 148.8, 129.2, 119.2, 110.6, 108.6, 55.8.

b) 1-(3',4'-Dimethoxyphenyl)ethylamine

3',4'-Dimethoxyacetophenone oxime (1 gram, 5.1 mmol) was dissolved in 10 milliliters of glacial acetic acid, the solution was flushed with $N_2$ and the palladium on carbon (0.2 grams, 5%) was added. The mixture was treated with 60 psi of $H_2$ in a Parr Type Shaker for 24 hours. The catalyst was filtered off and the filtrate was concentrated to afford a yellow oil which was taken up in water, basified to pH 12 with a saturated solution of sodium carbonate and extracted with methylene chloride. The combined extracts were dried over magnesium sulfate and concentrated to afford 1.97 grams (82%) of product as a yellow oil: $^1$H NMR (CDCl$_3$) δ7.02–6.75 (m, 3H), 4.08 (q, $J_1$=6.6 Hz, $J_2$=13.1 Hz, 1 H), 3.89 (s, 3H), 3.87 (s, 3H), 1.37 (d , J=6.6 Hz, 3H).

c) 1-Phthalimido-1-(3',4'-dimethoxyphenyl)ethane

To a stirred solution of 1-(3',4'dimethoxyphenyl) ethylamine (1.81 grams, 10.0 mmol) and sodium carbonate (1.14 grams, 10.8 mmol) in a mixture of water (80 milliliters) and acetonitrile (50 milliliters) was added N-carbethoxyphthalimide (2.19 grams, 10 mmol). The resulting suspension was stirred for 3.5 hours at room temperature and then filtered to afford 1.24 grams (40%) of crude product as a white powder. The crude product was recrystallized from hexane/ethyl acetate and dried in vacuo (60° C., <1 mm) to afford 0.85 grams (27%) of the product as white crystals: mp 124–125° C.; $^1$H NMR (DMSO-$d_6$) δ7.96–7.78 (m, 4H), 7.09–6.81 (m, 3H), 5.40 (q, J=7.2 Hz, 1H), 3.73 (s, 3H), 3.72(s, 3H), 1.81 (d, J=7.2 Hz, 3H); $^{13}$C NMR (DMSO-$d_6$) δ167.6, 148.4, 148.0, 134.4, 132.9, 131.3, 122.9, 118.8, 111.5, 110.8, 55.4, 48.6, 17.7. Anal. Calculated for $C_{18}H_{17}NO_4$. Theoretical: C, 69.44; H, 5.50; N, 4.50. Found: C, 69.63; H, 5.45; N, 4.42. HPLC 100%.

EXAMPLE 3

1-Phthalimido-1-(4'-methoxyphenyl)propane a) 4'-Methoxypropiophenone oxime

A solution of hydroxylamine hydrochloride (3.33 grams, 48 mmol) and sodium acetate (4.92 grams, 60 mmol) in 20 milliliters of water was added to a stirred solution of 4-methoxypropiophenone (5.26 grams, 30.0 mmol) in a mixture of water (30 milliliters) and ethanol (30 milliliters), a further 20 milliliters of ethanol was added to get a homogenous solution, which was stirred overnight. The resulting slurry was filtered, the filtrate was partially concentrated, to remove the ethanol and a white solid precipitated. The slurry was filtered and the solid was washed with water, and dried in vacuo (25° C., <1 mm) to afford 5.26 grams (98%) of product as a white solid: $^1$H NMR (CDCl$_3$) δ7.64–7.42 (m , 2H), 7.04–6.81(m, 2H), 3.82(s, 3H), 2.81(q , J=7.6 Hz), 2H), 1.17(t , J=7.6 Hz, 3H).

b) 1-(4'-Methoxyphenyl)propylamine

To a N$_2$ flushed solution of 4'-methoxypropiophenone oxime (4 grams, 22.3 mmol) in glacial acetic acid (40 milliliters) was added 0.8 grams of 5% Pd/C. The mixture was treated with 60 psi of H$_2$ in a Parr Type Shaker for 23 hours. The catalyst was filtered off through celite and the filtrate was concentrated to afford a yellow oil. The oil was taken up in water, the pH was adjusted to 12 using a saturated solution of sodium carbonate, and extracted with methylene chloride. The organic extract was dried over magnesium sulfate and concentrated to afford 3.04 grams (83%) of product as a yellow oil: $^1$H NMR (CDCl$_3$) δ7.32–7.20(m, 2H), 6.94–6.82(m, 2H), 3.79(s, 3H), 1.88–1.54(m, 4H), 0.87(t, J=7.4 Hz, 3H).

c) 1-Phthalimido-1-(4'-methoxyphenyl)propane

To a stirred solution of 1-(4'methoxyphenyl)propylamine (2.5 grams, 15.2 mmol) and sodium carbonate (1.74 grams, 16.4 mmol) in a mixture of water (50 milliliters) and acetonitrile (50 milliliters) was added N-carbethoxyphthalimide (3.34 grams, 15.2 mmol). The resulting suspension was stirred for 4.5 hours at room temperature, the acetonitrile was removed in vacuo and a solid formed. The slurry was filtered and the solid was washed with water and air dried to afford 1.73 grams (39%) of crude product as a white powder. The crude product was recrystallized from hexane/ethyl acetate and dried in vacuo (60° C., <1 mm) to afford 1.71 grams (38%) of the product as white crystals: mp 85–86° C.; $^1$H NMR (DMSO-$d_6$) δ7.92–7.79(m, 4H), 7.46–7.28(m,2 H), 6.97–6.83(m, 2 H), 5.19–5.06(m, 1 H), 3.72(s, 3H), 2.56–2.13(m, 2 H), 0.87(t, J=7.3 Hz, 3 H);$^{13}$C NMR (DMSO-$d_6$) δ167.8, 1.5, 134.6, 131.7, 131.0, 128.6, 123.1, 113.7, 55.2, 54.9, 23.8, 11.3. Anal. Calculated for $C_{18}H_{17}NO_3$. Theoretical: C,73.20; H,5.80; N, 4.74. Found: C,73.24; H, 5.74; N, 4.86. HPLC 100%.

EXAMPLE 4

1-Phthalimido-1-(3',4'-dimethoxyphenyl)methane

To a stirred solution of 3,4-dimethoxybenzylamine (0.836 grams, 5.00 mmol) and N-carbethoxyphthalimide (1.10 grams, 5.00 mmol) in 20 milliliters of tetrahydrofuran was added 1 drop of triethylamine and the mixture stirred overnight. After 24 hours at room temperature, the mixture was refluxed for 16 hours, then allowed to cool to room temperature without stirring. Crystals formed on cooling. The mixture was filtered, the solid dried in vacuo to afford 0.89 grams (60%) of 1-phthalimido-1-(3',4'-dimethoxyphenyl)methane as small white needles: mp 160–161° C.; $^1$H NMR (CDCl$_3$/TMS) δ7.8 (m, 2 H), 7.7 (m, 2 H), 7.03 (m, 2 H), 6.8 (m, 1 H), 4.78 (s, 2 H), 3.88 (s, 3 H, OCH$_3$), 3.84 (s, 3 H, OCH$_3$); $^{13}$C NMR (CDCl$_3$/TMS) δ168.0, 148.9, 148.7, 133.9, 132.1, 129.0, 123.3, 121.3, 112.1, 111.1, 55.9, 41.4. Anal. Calcd for $C_{17}H_{15}NO_4$. Theory C, 68.68; H, 5.09; N, 4.71. Found C, 68.49; H, 4.99; N, 4.67.

EXAMPLE 5

1-Phthalimido-(3,4-dimethoxyphenyl)toluene a) 1-Phenyl-1-(3,4-dimethoxyphenyl)methylamine To a stirring solution of 3,4-dimethoxybenzonitrile (1.63 grams, 10.0 mmol) in tetrahydrofuran (25 milliliters) was added phenyl magnesium bromide (3.7 milliliters, 3M, 11.0 mmol) and the resulting solution was refluxed for 40 minutes. The progress of the reaction was monitored by TLC (30% ethyl acetate/methylene chloride, UV), after 40 minutes the reaction was complete. The reaction mixture was allowed to cool and methanol (25 milliliters) was added slowly. When the effervescence had ceased sodium borohydride (0.40 grams, 10.5 mmol) was added slowly and the reaction mixture was stirred at room temperature overnight. The resulting dark purple mixture was extracted with ether (3 times with 50 milliliters) and the combined ether extracts back extracted into aqueous 3N hydrochloric acid (150 milliliters). The pH of the aqueous layer was then adjusted to 14 using sodium hydroxide (5 Molar) and the mixture was extracted with methylene chloride (2 times with 50 milliliters). The combined organic layers were dried over magnesium sulfate and concentrated in vacuo to afford 1.76 grams (72%) of product as an orange oil: $^1$H NMR (CDCl$_3$) δ7.43–7.16(m, 5H), 6.95–6.74(m, 3H), 5.17(s, 1H), 3.85(s, 3H), 3.84(s, 3H), 1.78(s, 2H).

b) A mixture of 1-phenyl-1-(3,4-dimethoxyphenyl) methylamine (0.73 grams, 3 mmol) and phthalic anhydride (0.44 grams, 3 mmol) were melted together and stirred for 5 minutes. After cooling, 1 gram of crude product formed as a yellow/orange glassy solid. The crude product was recrystallized from toluene and dried in vacuo (60° C., <1 mm) to afford 0.36 g (33%) of product as a white solid;$^1$H NMR (DMSO-$d_6$) δ12.96(s, 1H), 9.31–9.17(m, 1H), 7.85–6.73(m, 12H), 6.42–6.22(m, 1H), 3.72(s, 6H); $^{13}$C NMR (DMSO-$d_6$) δ167.7, 167.6, 148.5, 147.6, 142.7, 138.5, 134.8, 131.2, 130.5, 129.1, 128.9, 128.1, 127.8, 127.3, 126.6, 119.6, 111.5, 111.4, 55.7, 55.4, 55.4.

c) 1-Phthalimido-(3,4-dimethoxyphenyl)toluene

A solution of the product of step b) above (0.25 grams, 0.68 mmol) and sodium acetate (0.03 grams, 0.34 mmol) in acetic anhydride (6 milliliters) was refluxed for 30 minutes. The progress of the reaction was monitored by TLC (2% ethyl acetate/methylene chloride, UV) and reached completion after 30 minutes. The reaction mixture was cooled to room temperature, poured into iced water (20 milliliters) and stirred for 15 minutes. The mixture was extracted into methylene chloride (25 milliliters) and was washed successively with a saturated aqueous solution of sodium bicarbonate (15 milliliters), brine (10 milliliters), sodium bicarbonate (15 milliliters) and brine (10 milliliters). The organic layer was dried over magnesium sulfate and concentrated in vacuo to afford 0.19 grams of crude product as a orange oil. The crude product was purified by flash chromatography (silica gel, 10% ethyl acetate/methylene chloride) and dried in vacuo (25° C., <1 mm) to afford 0.15 grams (63%) of product as a slightly green colored solid: $^1$H NMR (CDCl$_3$) δ7.90–7.64(m, 4 H), 7.39–7.22(m, 5H), 7.07–6.91(m, 2 H), 6.88–6.76(m, 1 H), 6.66(s, 1 H), 3.87(s, 3 H), 3.80(s, 3 H); $^{13}$C NMR (CDCl$_3$) δ167.9, 148.8, 148.6, 138.3, 134.1, 131.9, 130.8, 128.3, 128.1, 127.5, 123.4, 121.6, 112.5, 110.7, 57.6, 55.9, 55.8.

EXAMPLE 6

1-Phthalimido-1-(3',4'-dimethoxyphenyl)pentane a) 3',4'-Dimethoxyvalerophenone

3',4'-Dimethoxyacetophenone (9.91 grams, 55 mmol) was added over 20 minutes to a cooled (0° C.) stirred solution of lithium diisopropylamide (28.9 milliliters, 2M, 57.8 mmol). After an additional 5 minutes the solution was cooled to −78° C. and 1-iodopropane (10.73 milliliters, 110 mmol) was rapidly added. The solution was allowed to slowly warm to room temperature and stirring was continued for 3 days. Reaction progress was monitored by TLC (30% , ethyl acetate/hexane, UV) and an equilibrium had been reached after three days between starting material (Rf=0.15), monoalkylated product (Rf=0.32) and dialkylated product (Rf=0.42). The reaction was treated with water (60 milliliters), ethyl acetate (100 milliliters) and a saturated solution of sodium bicarbonate (100 milliliters). The organic layer was separated and washed successively with 5% hydrochloric acid (100 milliliters) and saturated aqueous sodium bicarbonate (100 milliliters). The organic layer was dried over magnesium sulfate and concentrated to afford 15.17 grams of crude product as an orange oily liquid. The crude product was purified by flash chromatography (silica gel, 20% ethyl acetate/hexane) to afford 3.68 (25%) of the dialkylated product (3',4'-dimethoxy-2-propylvalerophenone) as a yellow solid and 1.01 grams (8%) of the monoalkylated product (3',4'-dimethoxyvalerophenone) as a yellow oily liquid: $^1$H NMR (CDCl$_3$) δ7.65–7.50 (m, 2H), 6.95–6.85(m, 1H), 3.95(s, 3 H), 3.94(s, 3 H), 2.99–2.88(m, 2 H), 1.81–1.64(m, 2 H), 1.52–1.34 (m, 2 H), 1.04–0.91(m, 3 H). $^{13}$C NMR (CDCl$_3$) δ199.1, 152.9, 148.8, 130.2, 122.5, 110.0, 109.8, 55.9, 55.8, 37.7, 26.7, 22.4, 13.8.

b) 3',4'-Dimethoxyvalerophenone oxime

To a stirred solution of 3',4'-dimethoxyvalerophenone (0.08 grams, 3.60 mmol) in a mixture of ethanol (25 milliliters) and water (5 milliliters) was added hydroxyamine hydrochloride (0.40 grams, 5.76 mmol) and sodium acetate (0.59 grams, 7.20 mmol) in water (5 milliliters). The solution was refluxed for two days. Reaction progress was monitored by TLC (20%, ethyl acetate/hexane, UV) and was complete after 2 days. The reaction was allowed to cool to ambient temperature and the ethanol was removed in vacuo to afford an oil/aqueous mixture. The mixture was extracted with methylene chloride. The dried extracts were concentrated in vacuo to afford 0.93 grams of crude product as a yellow oil. The crude product was purified by flash chromatography (silica gel, 20%, ethyl acetate/hexane) to afford 0.56 grams of product as a yellow oil: $^1$H NMR (CDCl$_3$) δ8.23–8.01(br s, 1H), 7.30–7.05(m, 2H), 6.93–6.81(m, 1H), 3.91(s, 3H), 3.90(s, 3H), 2.84–2.70 (m, 2H), 1.74–1.31(m, 4H), 0.93(t, J=7.2 Hz, 3H);$^{13}$ C NMR (CDCl$_3$) δ159.6, 150.1, 148.9, 128.5, 119.3, 110.6, 108.9, 55.9, 28.7, 25.6, 22.9, 13.8.

c) 1-(3',4'-Dimethoxyphenyl)pentylamine

To an N$_2$ flushed solution of 3',4'-dimethoxyvalerophenone oxime (0.5 grams, 2.1 mmol) in glacial acetic acid (10 milliliters) was added 0.1 grams of 5% Pd/C. The mixture was treated with 60 psi of H$_2$ in a Parr Type Shaker for 24 hours. The catalyst was filtered off through celite and the filtrate was concentrated in vacuo to afford a yellow oil. The oil was taken up in water, the pH was adjusted to 12 using a saturated solution of sodium carbonate, and extracted with methylene chloride. The organic extract was dried over magnesium sulfate and concentrated to afford 0.41 grams (87%) of product as a yellow oil: $^1$H NMR (CDCl$_3$) δ6.91–6.76(m, 3H), 3.98–3.78(m, 1H), 3.89(s, 3H), 3.87(s, 3H), 1.94–0.78(m, 11H).

d) 1-Phthalimido-1-(3',4'-dimethoxyphenyl)pentane

To a stirred solution of 1-(3',4'-dimethoxyphenyl)pentylamine (0.3 grams, 1.34 mmol) and sodium carbonate (0.15 grams, 1.45 mmol) in a mixture of water (10 milliliters) and acetonitrile (10 milliliters) was added N-carbethoxyphthalimide (0.29 grams, 1.34 mmol). The resulting solution was stirred for 3 hours at room temperature, the acetonitrile was evaporated and a two phase mixture resulted. The organic phase was extracted into methylene chloride, dried over magnesium sulfate and concentrated to afford 0.41 grams of crude product as an oil. The crude product was purified by flash chromatography (silica gel, 30% ethyl acetate/hexane) to afford 0.18 grams (38%) of the product as an oil: $^1$H NMR (CDCl$_3$) δ7.88–7.63(m, 4H), 7.20–7.07(m, 2H),6.82–6.76(m, 1H), 5.34–5.18(m, 1H), 3.89(s, 3H), 3.85(s, 3H),2.66–2.43(m, 1H),2.40–2.17 (m, 1H), 1.50–1.20(m, 2H), 0.96–0.81(m, 3H). $^{13}$C NMR (CDCl$_3$) δ1.68.5, 148.8, 148.5, 133.8, 132.5, 131.9, 123.1, 120.6, 111.6, 110.8, 55.9, 55.8, 55.0, 30.9, 29.2, 22.3, 13.9.

EXAMPLE 7

1-Phthalimido-1-(3',4'-dimethoxyphenyl)-2-propylpentane a) 3',4'-Dimethoxy-2-propylvalerophenone 3',4'-Dimethoxyacetophenone (9.91 grams, 55 mmol) was added over 20 minutes to a cooled (0° C.) stirred solution of lithium diisopropylamide (28.9 milliliters, 2M, 57.8 mmol). After an additional 5 minutes the solution was cooled to −78° C. and 1-iodopropane (10.73 milliliters, 110 mmol) was rapidly added. The solution was allowed to slowly warm to room temperature and stirring was continued for 3 days. Reaction progress was monitored by TLC (30%, ethyl acetate/hexane, UV) and an equilibrium had been reached after three days between starting material (Rf=0.15), monoalkylated product (Rf=0.32) and dialkylated product (Rf=0.42). The reaction was treated with water (60 milliliters), ethyl acetate (100 milliliters) and a saturated solution of sodium bicarbonate (100 milliliters). The organic layer was separated and washed successively with 5% HCl (100 milliliters) and saturated aqueous sodium bicarbonate (100 milliliters). The organic layer was dried over magnesium sulfate and concentrated to afford 15.17 grams of crude product as an orange oily liquid. The crude product was purified by flash chromatography (silica gel, 20% ethyl acetate/hexane) to afford 3.68 (25%) of the dialkylated product (3',4'-dimethoxy-2-propylvalerophenone) as a yellow solid and 1.01 grams (8%) of the monoalkylated product (3',4'-dimethoxyvalerophenone) as a yellow oily liquid: mp 55.5–56.5° C., $^1$H NMR (CDCl$_3$) δ7.67–7.54(m, 2 H), 6.96–6.86(m, 1 H), 3.95(s, 3 H), 3.93(s, 3 H), 3.52–3.36(m, 1 H), 1.86–1.17(m, 8 H), 0.96–0.80(m, 6 H). $^{13}$C NMR (CDCl$_3$) δ203.4, 143.1, 149.1, 131.0, 122.6, 110.3, 109.9, 56.0, 55.9, 45.1, 35.1, 20.9, 14.3.

b) 3',4'-Dimethoxy-2-propyl-valerophenone oxime

To a stirred solution of 3',4'-dimethoxy-2-propylvalerophenone (2.64 grams, 10 mmol) in a mixture of ethanol (45 milliliters) and water (10 milliliters) was added hydroxyamine hydrochloride (1.11 grams, 16 mmol) and sodium acetate (1.64 grams, 20 mmol) in water (10 milliliters). The solution was refluxed for 1 week. Reaction progress was monitored by TLC (30%, ethyl acetate/hexane, UV) and had reached an equilibrium after 1 week. The reaction was allowed to cool to ambient temperature and the ethanol was removed in vacuo to afford an oil/aqueous mixture which was extracted with methylene chloride, dried over magnesium sulfate and concentrated in vacuo to afford 2.93 grams of crude product as a yellow oil. The crude product was purified by flash chromatography (silica gel, 30%, ethyl acetate/hexane) to afford 1.28 grams (46%) of product as a yellow oil. $^1$H NMR (CDCl$_3$) δ7.10–6.75(m, 3H), 3.78–3.96(m, 6H), 3.49–3.31(m, 0.5H), 2.65–2.50 (m, 0.5H), 1.91–1.19(m, 8H), 1.01–0.81(m, 6H). $^{13}$C NMR (CDCl$_3$) δ162.5, 161.5, 149.5, 149.0, 148.6, 129.4, 125.9, 120.2, 111.2, 110.6, 110.5, 55.9, 55.8, 45.1, 38.9, 34.8, 21.3, 20.5, 14.2.

c) 1-(3',4'-Dimethoxyphenyl)-2-propylpentylaimine

To an N$_2$ flushed solution of 3',4'-dimethoxy-2-propyl-valerophenone (1.0 grams, 3.6 mmol) in glacial acetic acid (20 milliliters) was added 0.2 grams of 5% Pd/C. The mixture was treated with 60 psi of H$_2$ in a Parr Type Shaker for 24 hours. Reaction progress was monitored by TLC (30% ethyl acetate/hexane, UV) some starting material remained after 24 hours. A further 0.4 grams of 10% Pd/C was added and the mixture was treated with 60 psi of H$_2$ in a Parr Type Shaker for 24 hours. The catalyst was filtered off through celite and the filtrate was concentrated to afford a yellow oil. The oil was taken up in water, the pH was adjusted to 12 using a saturated solution of sodium carbonate, and extracted with methylene chloride. The organic extract was dried over magnesium sulfate and concentrated in vacuo to afford 0.51grams (57%) of product as a yellow oil: $^1$H NMR (CDCl$_3$) δ6.91–6.74(m, 3H), 3.95–3.78(m, 1H), 3.89(s, 3H), 3.87(s, 3H), 1.67–0.75(m, 17H).

d) 1-Phthalimido-1-(3',4'-dimethoxyphenyl)-2-propylpentane

To a stirred solution of 1-(3',4'-dimethoxyphenyl)-2-propylpentylamine (0.40 grams, 1.60 mmol) and sodium carbonate (0.18 grams, 1.72 mmol) in a mixture of water (5 milliliters) and acetonitrile (10 milliliters) was added N-carbethoxyphthalimide (0.35 grams, 1.60 mmol). The resulting solution was stirred for 2.5 hours at room temperature, the acetonitrile was evaporated and a two phase mixture resulted. The organic phase was extracted into methylene chloride, dried over magnesium sulfate and concentrated in vacuo to afford 0.6 grams of crude product as an oil. The crude product was purified by flash chromatography (silica gel, 25% ethyl acetate/hexane) to afford 0.25 grams of the product as an oil which after a few days solidified. The white solid was dried in vacuo (60° C., <1 mm) to afford 0.24 grams of pure product as a white solid: mp 100–101° C.; $^1$H NMR (CDCl$_3$) δ7.84–7.59(m, 4H), 7.27–7.02(m, 2H), 6.81–6.68(m, 1H), 5.01(d, J=12 Hz, 1H), 3.89(s, 3H), 3.84(s, 3H), 3.17–2.98(m, 1H), 1.49–0.66(m, 14H). $^{13}$C NMR (CDCl$_3$) δ168.5, 148.7, 148.4, 133.8, 131.9, 131.8, 123.1, 121.6, 112.0, 110.7, 58.9, 55.9, 55.7, 36.2, 31.9, 31.8, 18.7, 18.1, 14.6, 14.3.

Anal. Calcd. for C$_{24}$H$_{29}$NO$_4$. Theoretical: C, 72.87; H, 7.40; N, 3.54. Found: C, 72.70; H, 7.40; N, 3.51.

EXAMPLE 8

Tablets, each containing 50 milligrams of active ingredient, can be prepared in the following manner:

| Constituents (for 1000 tablets) | |
|---|---|
| active ingredient | 50.0 grams |
| lactose | 50.7 grams |
| wheat starch | 7.5 grams |
| polyethylene glycol 6000 | 5.0 grams |
| talc | 5.0 grams |
| magnesium stearate | 1.8 grams |
| demineralized water | q.s. |

The solid ingredients are first forced through a sieve of 0.6 mm mesh width. The active ingredient, the lactose, the talc, the magnesium stearate and half of the starch then are mixed. The other half of the starch is suspended in 40 milliliters of water and this suspension is added to a boiling solution of the polyethylene glycol in 100 milliliters of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 9

Tablets, each containing 100 milligrams of active ingredient, can be prepared in the following manner:

| Constituents (for 1000 tablets) | |
|---|---|
| active ingredient | 100.0 grams |
| lactose | 100.0 grams |
| wheat starch | 47.0 grams |
| magnesium stearate | 3.0 grams |

All the solid ingredients are first forced through a sieve of 0.6 mm mesh width. The active ingredient, the lactose, the magnesium stearate and half of the starch then are mixed. The other half of the starch is suspended in 40 milliliters of water and this suspension is added to 100 milliliters of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 10

Tablets for chewing, each containing 75 milligrams of active ingredient, can be prepared in the following manner:

| Composition (for 1000 tablets) | |
|---|---|
| active ingredient | 75.0 grams |
| mannitol | 230.0 grams |
| lactose | 150.0 grams |
| talc | 21.0 grams |
| glycine | 12.5 grams |
| stearic acid | 10.0 grams |
| saccharin | 1.5 grams |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. The active ingredient, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

EXAMPLE 11

Tablets, each containing 10 milligrams of active ingredient, can be prepared in the following manner:

| Composition (for 1000 tablets) | |
|---|---|
| active ingredient | 10.0 grams |
| lactose | 328.5 grams |
| corn starch | 17.5 grams |
| polyethylene glycol 6000 | 5.0 grams |
| talc | 25.0 grams |
| magnesium stearate | 4.0 grams |
| demineralized water | q.s. |

The solid ingredients are first forced through a sieve of 0.6 mm mesh width. Then the active ingredient, lactose, talc, magnesium stearate and half of the starch are intimately mixed. The other half of the starch is suspended in 65 milliliters of water and this suspension is added to a boiling solution of the polyethylene glycol in 260 milliliters of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 12

Gelatin dry-filled capsules, each containing 100 milligrams of active ingredient, can be prepared in the following manner:

| Composition (for 1000 capsules) | |
|---|---|
| active ingredient | 100.0 grams |
| microcrystalline cellulose | 30.0 grams |
| sodium lauryl sulphate | 2.0 grams |
| magnesium stearate | 8.0 grams |

The sodium lauryl sulphate is sieved into the active ingredient through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 milligrams each into size 0 (elongated) gelatin dry-fill capsules.

EXAMPLE 13

A 0.2% injection or infusion solution can be prepared, for example, in the following manner:

| active ingredient | 5.0 grams |
|---|---|
| sodium chloride | 22.5 grams |
| phosphate buffer pH 7.4 | 300.0 grams |
| demineralized water | to 2500.0 milliliters |

The active ingredient is dissolved in 1000 milliliters of water and filtered through a microfilter. The buffer solution is added and the whole is made up to 2500 milliliters with water. To prepare dosage unit forms, portions of 1.0 or 2.5 milliliters each are introduced into glass ampoules (each containing respectively 2.0 or 5.0 milligrams of active ingredient).

What is claimed is:

1. A compound of the formula:

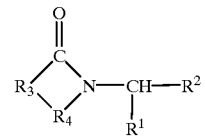

wherein $R^1$ is phenyl which is substituted with one or more substituents each independently selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo;

$R^2$ is alkyl of 1 to 10 carbon atoms, phenyl, pyridyl, heterocyclyl, —$CH_2$-aryl, or —$CH_2$-heterocycle;

$R^3$ is
  (i) ethylene,
  (ii) vinylene,
  (iii) vicinal alkylene of 3 to 10 carbon atoms,
  (iv) vicinal alkenylene of 3 to 10 carbon atoms,
  (v) cycloalkylene of 4 to 9 carbon atoms, unsubstituted or substituted with 1 to 2 substituents each selected independently from the group consisting of nitro, cyano, trifluoromethyl, carbethoxy, carbomethoxy, carbopropoxy, acetyl, carbamoyl, acetoxy, carboxy, hydroxy, amino, substituted amino alkyl of 1 to 4 carbon atoms, alkoxy of 1 to 4 carbon atoms, and halo, (vi) cycloalkenylene of 4 to 9 carbon atoms unsubstituted or substituted with 1 to 2 substituents each selected independently from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 4 carbon atoms, alkoxy of 1 to 4 carbon atoms, and halo, or (vii) o-phenylene unsubstituted or substituted with 1 to 2 substituents each selected independently from the group consisting of nitro, cyano, trifluoromethyl, carbethoxy, carbomethoxy, carbopropoxy, acetyl, carbamoyl, acetoxy, carboxy, hydroxy, amino, substituted amino alkyl of 1 to 4 carbon atoms, alkoxy of 1 to 4 carbon atoms, and halo; and $R^4$ is —CH$_2$— or —CX in which X is O or S.

2. A compound of the formula:

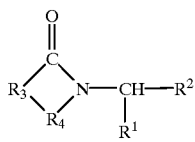

wherein $R^1$ is phenyl which is substituted with two substituents each independently selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo;

$R^2$ is alkyl of 1 to 10 carbon atoms, phenyl, or benzyl;

$R^3$ is o-phenylene unsubstituted or substituted with 1 to 2 substituents each selected independently from the group consisting of nitro, cyano, trifluoromethyl, carbethoxy, carbomethoxy, carbopropoxy, acetyl, carbamoyl, acetoxy, carboxy, hydroxy, amino, substituted amino alkyl of 1 to 4 carbon atoms, alkoxy of 1 to 4 carbon atoms, and halo; and $R^4$ is —CH$_2$— or —CO.

3. A compound according to claim 2 wherein $R^1$ is phenyl which is substituted in each of the 3- and 4-positions with alkoxy of 1 to 10 carbon atoms.

4. A compound according to claim 3 wherein $R^4$ is —CH$_2$—.

5. A compound according to claim 3 wherein $R^4$ is —CO—.

6. A compound according to claim 1 wherein $R^4$ is —CO.

7. A compound according to claim 6 wherein $R^1$ is 3,4-dimethoxyphenyl.

8. A compound according to claim 6 wherein $R^2$ is methyl.

9. A compound according to claim 6 wherein $R^2$ is ethyl.

10. A compound according to claim 6 wherein $R^2$ is phenyl.

11. A compound according to claim 6 wherein $R^2$ is benzyl.

12. A compound according to claim 6 wherein $R^2$ is hept-4-yl.

13. A compound according to claim 6 wherein $R^2$ is methoxyphenyl.

14. A compound according to claim 6 wherein $R^3$ is o-phenylene.

15. A compound according to claim 1 which is selected from the group consisting of 1-phthalimido-1-(3,4-diethoxyphenyl)ethane, 1-(1-oxoisoindolinyl)-1-(3,4-diethoxyphenyl)ethane, 1-phthalimido-1-(3,4-diethoxyphenyl)propane, 1-(1-oxoisoindolinyl)-1-(3,4-diethoxyphenyl)propane, 1-phthalimido-1-(3,4-diethoxyphenyl)butane, 1-(1-oxoisoindolinyl)-1-(3,4-diethoxyphenyl)butane, 1-phthalimido-1-(3,4-diethoxyphenyl)-2-phenylethane, 1-(1-oxoisoindolinyl)-1-(3,4-diethoxyphenyl)-2-phenylethane, 1-phthalimido-1-(3,4-diethoxyphenyl)-3-pyridylpropane, 1-(1-oxoisoindolinyl)-1-(3,4-diethoxyphenyl)-3-pyridylpropane, 1-phthalimido-1-(3,4-diethoxyphenyl)-3-phenylpropane, 1-(1-oxoisoindolinyl)-1-(3,4-diethoxyphenyl)-3-phenylpropane, 1-phthalimido-1-(3,4-diethoxyphenyl)-2-pyridylethane, 1-(1-oxoisoindolinyl)-1-(3,4-diethoxyphenyl)-2-pyridylethane, 1-phthalimido-1-(3,4-diethoxyphenyl)butane, 1-(1-oxoisoindolinyl)-1-(3,4-diethoxyphenyl)butane, 1-phthalimido-1-(3,4-diethoxyphenyl)-2-imidazolylethane, 1-(1-oxoisoindolinyl)-1-(3,4-diethoxyphenyl)-2-imidazolylethane, 1-phthalimido-1-(3,4-diethoxyphenyl)-3-methylbutane, and 1-(1-oxoisoindolinyl)-1-(3,4-diethoxyphenyl)-3-methylbutane.

16. A pharmaceutical composition comprising an amount of a compound according to claim 1 effective upon single or multiple dosage to inhibit TNFa in combination with a pharmaceutical carrier.

17. A pharmaceutical composition comprising an amount of a compound according to claim 2 effective upon single or multiple dosage to inhibit TNFa in combination with a pharmaceutical carrier.

18. A compound according to claim 1 wherein $R^3$ is o-phenylene.

* * * * *